(12) United States Patent
Freyman et al.

(10) Patent No.: US 8,114,049 B2
(45) Date of Patent: Feb. 14, 2012

(54) BALLOON CATHETER DEVICES WITH FOLDED BALLOONS

(75) Inventors: Toby Freyman, Waltham, MA (US); Gordon Kocur, Lino Lakes, MN (US); Daniel Horn, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 134 days.

(21) Appl. No.: 12/399,548

(22) Filed: Mar. 6, 2009

(65) Prior Publication Data
US 2009/0227949 A1 Sep. 10, 2009

Related U.S. Application Data

(60) Provisional application No. 61/034,328, filed on Mar. 6, 2008.

(51) Int. Cl.
*A61M 31/00* (2006.01)
*A61M 37/00* (2006.01)
*A61M 29/00* (2006.01)

(52) U.S. Cl. ............ 604/103.08; 604/103.02; 604/96.01

(58) Field of Classification Search .................. 604/509, 604/95.03, 101.01–101.05, 96.01, 103, 103.02, 604/103.08; 606/191–195
See application file for complete search history.

(56) References Cited

U.S. PATENT DOCUMENTS

| | | |
|---|---|---|
| 4,417,576 A | 11/1983 | Baran |
| 4,423,725 A | 1/1984 | Baran et al. |
| 4,994,033 A | 2/1991 | Shockey et al. |
| 4,994,072 A | 2/1991 | Bhate et al. |
| 5,015,231 A | 5/1991 | Keith et al. |
| 5,042,976 A | 8/1991 | Ishitsu et al. |
| 5,049,132 A | 9/1991 | Shaffer et al. |
| 5,091,205 A | 2/1992 | Fan |
| 5,092,841 A | 3/1992 | Spears |
| 5,100,386 A | 3/1992 | Inoue |
| 5,102,402 A * | 4/1992 | Dror et al. ............... 604/265 |
| 5,141,494 A | 8/1992 | Danforth et al. |
| 5,195,969 A | 3/1993 | Wang et al. |
| 5,196,024 A | 3/1993 | Barath |

(Continued)

FOREIGN PATENT DOCUMENTS

DE 203 21 514 U1 11/2007

(Continued)

OTHER PUBLICATIONS

Communication Relating to the Results of the Partial International Search, from PCT/US2009/036354, mailed May 26, 2009.

(Continued)

*Primary Examiner* — Nicholas Lucchesi
*Assistant Examiner* — Rebecca E Eisenberg
(74) *Attorney, Agent, or Firm* — Kenyon & Kenyon LLP

(57) ABSTRACT

Catheter devices having an expandable balloon for delivering a therapeutic agent to a body site. The balloon has one or more folds which serve as a reservoir for containing the therapeutic agent. The fold may have any of various configurations to hold the therapeutic agent. In some cases, the balloon comprises one or more lobes that forms the fold(s). The therapeutic agent may be provided in various ways. For example, the therapeutic agent may be contained in packets that rupture upon expansion of the balloon, or as a plurality of discrete bulk masses, or sealed within compartments.

15 Claims, 11 Drawing Sheets

U.S. PATENT DOCUMENTS

| | | | |
|---|---|---|---|
| 5,213,576 A | 5/1993 | Abiuso et al. |
| 5,226,913 A | 7/1993 | Pinchuk |
| 5,232,444 A | 8/1993 | Just et al. |
| 5,292,321 A | 3/1994 | Lee |
| 5,295,959 A | 3/1994 | Gurbel et al. |
| 5,304,121 A | 4/1994 | Sahatjian |
| 5,320,604 A | 6/1994 | Walker et al. |
| 5,324,261 A | 6/1994 | Amundson et al. |
| 5,348,538 A | 9/1994 | Wang et al. |
| 5,352,236 A | 10/1994 | Jung et al. |
| 5,364,356 A | 11/1994 | Hofling |
| 5,370,614 A | 12/1994 | Amundson et al. |
| 5,383,928 A | 1/1995 | Scott et al. |
| 5,397,307 A | 3/1995 | Goodin |
| 5,447,497 A | 9/1995 | Sogard et al. |
| 5,456,666 A | 10/1995 | Campbell et al. |
| 5,464,650 A | 11/1995 | Berg et al. |
| 5,498,238 A | 3/1996 | Shapland et al. |
| 5,499,971 A | 3/1996 | Shapland et al. |
| 5,501,662 A | 3/1996 | Hofmann |
| 5,505,700 A | 4/1996 | Leone et al. |
| 5,507,724 A | 4/1996 | Hofmann et al. |
| 5,545,132 A | 8/1996 | Fagan et al. |
| 5,545,208 A | 8/1996 | Wolff et al. |
| 5,562,922 A | 10/1996 | Lambert |
| 5,571,086 A | 11/1996 | Kaplan et al. |
| 5,599,306 A | 2/1997 | Klein et al. |
| 5,624,411 A | 4/1997 | Tuch |
| 5,626,600 A | 5/1997 | Horzewski et al. |
| 5,634,901 A | 6/1997 | Alba et al. |
| 5,653,689 A | 8/1997 | Buelna et al. |
| 5,674,192 A | 10/1997 | Sahatjian et al. |
| 5,679,400 A | 10/1997 | Tuch |
| 5,693,014 A | 12/1997 | Abele et al. |
| 5,704,908 A | 1/1998 | Hofmann et al. |
| 5,707,358 A | 1/1998 | Wright |
| 5,707,385 A | 1/1998 | Williams |
| 5,738,901 A | 4/1998 | Wang et al. |
| 5,746,745 A | 5/1998 | Abele et al. |
| 5,749,915 A | 5/1998 | Slepian |
| 5,810,870 A | 9/1998 | Myers et al. |
| 5,833,651 A | 11/1998 | Donovan et al. |
| 5,833,659 A | 11/1998 | Kranys |
| 5,843,089 A | 12/1998 | Sahatjian et al. |
| 5,893,840 A | 4/1999 | Hull et al. |
| 5,941,871 A | 8/1999 | Adams et al. |
| 5,947,925 A | 9/1999 | Ashiya et al. |
| 5,964,730 A | 10/1999 | Williams et al. |
| 6,129,706 A | 10/2000 | Janacek |
| 6,135,982 A | 10/2000 | Campbell |
| 6,149,641 A | 11/2000 | Ungs |
| 6,280,411 B1 | 8/2001 | Lennox |
| 6,364,856 B1 | 4/2002 | Ding et al. |
| 6,369,039 B1 | 4/2002 | Palasis et al. |
| 6,450,989 B2 | 9/2002 | Dubrul et al. |
| 6,517,514 B1 | 2/2003 | Campbell |
| 6,544,221 B1 | 4/2003 | Kokish et al. |
| 6,544,223 B1 | 4/2003 | Kokish |
| 6,547,803 B2 | 4/2003 | Seward et al. |
| 6,593,130 B1 | 7/2003 | Sen et al. |
| 6,638,246 B1 | 10/2003 | Naimark et al. |
| 6,652,581 B1 | 11/2003 | Ding |
| 6,656,155 B2 | 12/2003 | Freyman |
| 6,656,162 B2 | 12/2003 | Santini, Jr. et al. |
| 6,743,388 B2 | 6/2004 | Sridharan et al. |
| 6,765,059 B2 | 7/2004 | Corley |
| 6,796,958 B2 | 9/2004 | Chen et al. |
| 6,939,320 B2 | 9/2005 | Lennox |
| 6,991,617 B2 | 1/2006 | Hektner et al. |
| 7,048,714 B2 | 5/2006 | Richter |
| 7,081,113 B2 | 7/2006 | Sutton |
| 7,166,099 B2 | 1/2007 | Devens, Jr. |
| 7,364,585 B2 | 4/2008 | Weber |
| 7,572,625 B2 | 8/2009 | Davis et al. |
| 2004/0049259 A1 | 3/2004 | Strecker |
| 2004/0127978 A1 | 7/2004 | Sparer et al. |
| 2004/0181252 A1 | 9/2004 | Boyle et al. |
| 2004/0215227 A1 | 10/2004 | McMorrow et al. |
| 2005/0015046 A1 | 1/2005 | Weber et al. |
| 2005/0182361 A1 | 8/2005 | Lennox |
| 2005/0228417 A1 | 10/2005 | Teitelbaum et al. |
| 2005/0273049 A1 | 12/2005 | Krulevitch et al. |
| 2006/0079836 A1 | 4/2006 | Holman et al. |
| 2006/0167407 A1 | 7/2006 | Weber et al. |
| 2006/0184112 A1 | 8/2006 | Horn et al. |
| 2006/0190022 A1 | 8/2006 | Beyar et al. |
| 2007/0106215 A1 | 5/2007 | Olsen et al. |
| 2007/0184085 A1 | 8/2007 | Radhakrishnan et al. |
| 2008/0021385 A1 | 1/2008 | Barry et al. |
| 2008/0140002 A1 | 6/2008 | Ramzipoor et al. |
| 2009/0227948 A1 | 9/2009 | Chen et al. |
| 2009/0227949 A1 | 9/2009 | Knapp et al. |
| 2011/0054396 A1 | 3/2011 | Kangas et al. |

FOREIGN PATENT DOCUMENTS

| | | |
|---|---|---|
| EP | 0712615 A1 | 5/1996 |
| EP | 0835673 A2 | 4/1998 |
| EP | 1 062 966 A1 | 12/2000 |
| EP | 1462127 A1 | 9/2004 |
| EP | 1 595 569 A2 | 11/2005 |
| SU | 1069826 A1 | 1/1984 |
| WO | 94/23787 A1 | 10/1994 |
| WO | 96/00597 A1 | 1/1996 |
| WO | 9949908 | 10/1999 |
| WO | 03/011363 A2 | 2/2003 |
| WO | 2004060471 | 7/2004 |
| WO | 2005/027996 A2 | 3/2005 |
| WO | 2005037339 | 4/2005 |
| WO | 2005/113058 A1 | 12/2005 |
| WO | 2006/042260 A2 | 4/2006 |
| WO | 2006138013 | 12/2006 |
| WO | 2007/055732 A1 | 5/2007 |
| WO | 2007/090385 A2 | 8/2007 |
| WO | 2007/117755 A2 | 10/2007 |
| WO | 2008/021019 A2 | 2/2008 |
| WO | 2008021025 A1 | 2/2008 |
| WO | 2008086794 A2 | 7/2008 |
| WO | 2009005933 | 1/2009 |
| WO | 2009/046206 A1 | 4/2009 |
| WO | 2009121565 A2 | 10/2009 |

OTHER PUBLICATIONS

International Search Report and Written Opinion of the International Searching Authority, from PCT/US2009/036354, mailed Jul. 2, 2009.

European Patent Office, International Search Report and Written Opinion of the International Searching Authority, from related International Application No. PCT/US2009/036359, mailed Jun. 16, 2009.

Kito, H., et al., "A Total Delivery System of Genetically Engineered Drugs or Cells for Diseased Vessels -Concept, Materials, and Fabricated Protitype Device," ASAIO Journal 1994, vol. 40, No. 3, M260-M266.

Annex to Form PCT/ISA/206—Communication Relating to the Results of the Partial International Search, mailed Dec. 28, 2010, from related International Application No. PCT/US2010/045877.

International Search Report and Written Opinion of the International Searching Authority, mailed Feb. 15, 2011, from related International Application No. PCT/US2010/045877.

International Search Report and Written Opinion of the International Searching Authority, from related International Application No. PCT/US2009/036349, mailed May 18, 2010.

* cited by examiner

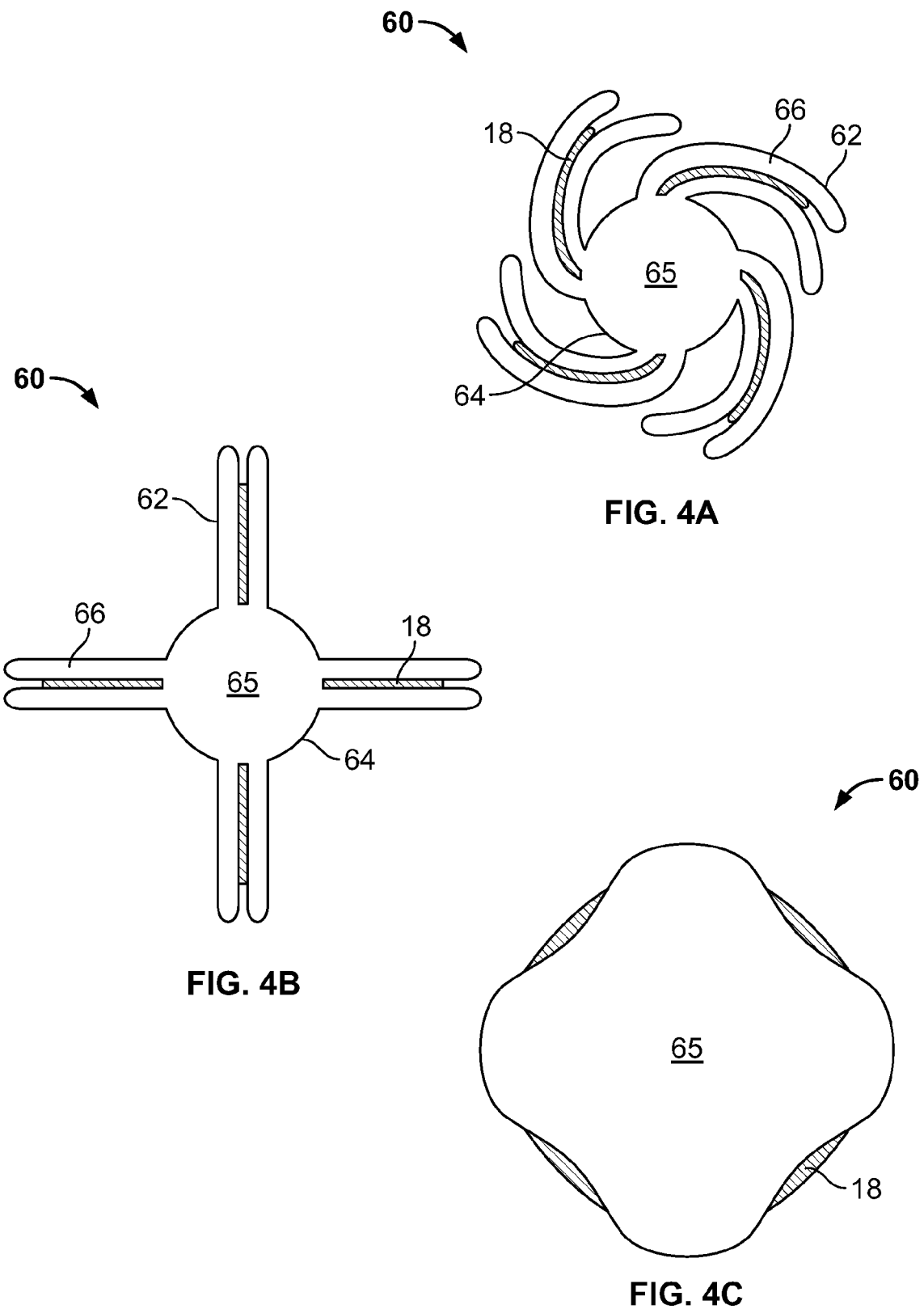

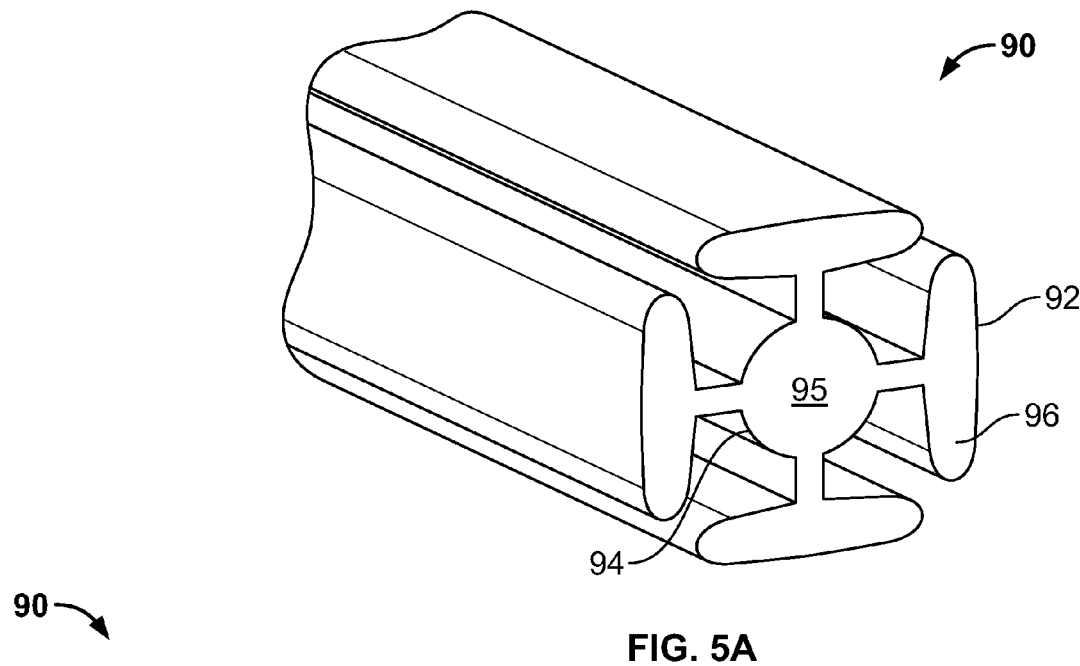
FIG. 5A
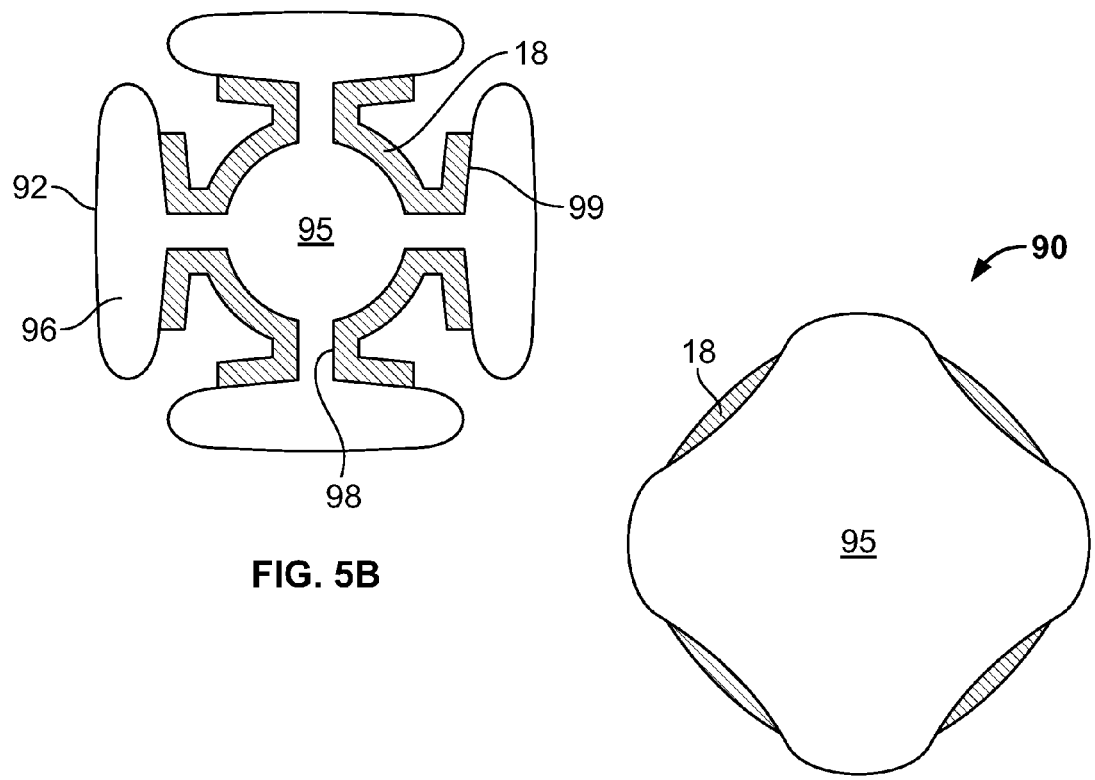
FIG. 5B
FIG. 5C

US 8,114,049 B2

BALLOON CATHETER DEVICES WITH FOLDED BALLOONS

RELATED APPLICATIONS

This application claims the benefit of provisional application Ser. No. 61/034,328 (filed 6 Mar. 2008), which is incorporated by reference herein.

TECHNICAL FIELD

The present invention relates to medical devices, more particularly, to catheter devices.

BACKGROUND

Catheters are used in a wide variety of minimally-invasive or percutaneous medical procedures. Balloon catheters having drug coatings may be used to treat diseased portions of blood vessels. Typically, the balloon is inserted through a peripheral blood vessel and then guided via a catheter through the vascular system to the target intravascular site. However, as the balloon travels through the vascular system, the flow of blood may wash away some of the drug coating. In addition, the control of the timing, location, and/or duration of the drug release can be an issue. Therefore, there is a need for improved catheter-based devices for drug delivery to an intravascular site.

SUMMARY

In one embodiment, the present invention provides a medical device comprising: a catheter; a balloon mounted on the catheter, the balloon having a main body and at least one lobe that forms a fold, wherein the fold opens upon expansion of the balloon; and a therapeutic agent disposed within the fold, wherein opening of the fold upon expansion of the balloon promotes the release of the therapeutic agent.

In another embodiment, the present invention provides a medical device comprising: a catheter; a balloon mounted on the catheter, the balloon comprising at least one lobe forming a fold of the balloon, wherein the fold opens upon expansion of the balloon; and a packet disposed within the fold, the packet containing a therapeutic agent and having a first attachment site where the packet is attached to the lobe and a second attachment site where the packet is attached to an adjacent surface of the balloon.

In another embodiment, the present invention provides a medical device comprising: a catheter; a balloon mounted on the catheter, the balloon having a plurality of folds that open upon expansion of the balloon; and a plurality of discrete bulk masses of therapeutic agent disposed within the folds, wherein the bulk masses of therapeutic agent are released upon opening of the folds.

BRIEF DESCRIPTION OF THE DRAWINGS

FIG. 1A shows the catheter device with the balloon in a deflated state. FIG. 1B shows an enlarged, cross-section view of a folded groove of the balloon. FIG. 1C shows the catheter device with the balloon inflated.

FIG. 2A shows the catheter device with the balloon in a deflated state. FIG. 2B shows the catheter device with the balloon inflated.

FIG. 3A shows the catheter device with the balloon in a deflated state. FIG. 3B shows the catheter device with the balloon inflated.

FIGS. 4A-4C show transverse cross-section views of a balloon according to another embodiment. FIG. 4A shows the balloon in a deflated state. FIG. 4B shows the balloon partially inflated. FIG. 4C shows the balloon fully inflated.

FIGS. 5A-5C show a balloon according to another embodiment. FIG. 5A shows a perspective view of the balloon in a deflated state. FIG. 5B shows a transverse, cross-section view of the balloon in FIG. 5A. FIG. 5C shows the balloon fully inflated.

FIG. 6A shows the balloon in a deflated state. FIG. 6B shows the balloon in a fully inflated state.

FIGS. 12A (side view), 12B (transverse cross-section view), and 12C (enlarged, cross-section view of a compartment) show the balloon in a deflated state. FIGS. 12D (side view) and 12E (enlarged, cross-section view of a compartment) show the balloon in an inflated state.

DETAILED DESCRIPTION

Catheter devices of the present invention use an expandable balloon for delivering a therapeutic agent to a target site in the body. The balloon is designed to be insertable in the body via a catheter. The therapeutic agent can be associated with the balloon in any of various ways, as further described below. Any of various mechanisms conventionally used for the delivery, actuation, or expansion (e.g., by inflation) of balloon catheter devices may be used in the present invention. The balloon catheter may be designed similar to those that have been known in the art, including but not limited to angioplasty catheters, stent delivery catheters, inflation catheters, and/or perfusion catheters. The catheter devices of the present invention may be used in conjunction with other drug delivery devices, such as stents.

The balloon has one or more folds which serve as reservoirs for containing a therapeutic agent. The folds may be oriented in any of various ways on the balloon, including, for example, longitudinally, radially, circumferentially, or helically. The folds may be made by any of the methods known in the art, including but not limited to methods described in U.S. Pat. No. 5,342,307 (Enteneuer et al.), 5,147,302 (Enteneuer et al.), 5,458,572 (Campbell et al.), 5,954,740 (Ravenscroft et al.), 6,013,055 (Bampos et al.), 7,128,868 (Eidenschink), or 7,306,616 (Eidenschink et al.), 2004/0215227 (McMorrow et al.), which are all incorporated by reference herein.

The folds may have any of various configurations to hold the therapeutic agent. For example, the folds may be in the form of pockets, grooves, dimples, or wells. The folds are not limited to structures formed by the bending, creasing, or pleating of the balloon wall. Folds may also be formed as voids within the balloon wall itself (e.g., as grooves, channels, or trenches), which may be made during extrusion or by etching, stamping, laser ablation, or heat ablation of the balloon.

Figure 1A:
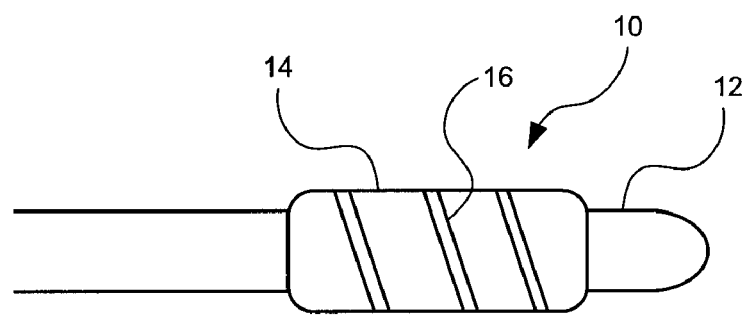
FIGS. 1A-1C show a catheter device according to an embodiment of the present invention.
Figure 1B:
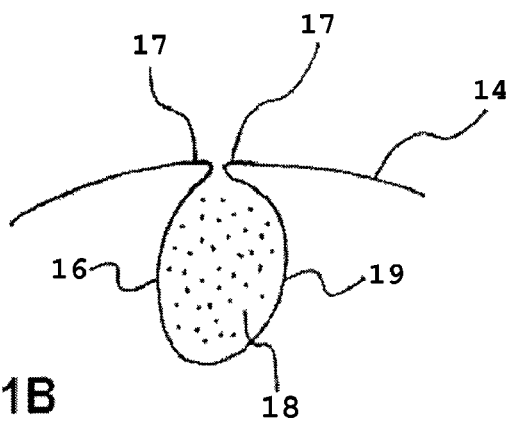

As the balloon is expanded (e.g., by inflation), the folds are made to open such that the therapeutic agent is exposed and allowed to be released. For example, referring to the embodiment shown in FIGS. 1A-1C, a catheter device 10 comprises a balloon 14 mounted on an elongate shaft 12. Balloon 14 has a folded groove 16 extending in a helical fashion around the circumference of balloon 14. As shown in the enlarged, cross-section view in FIG. 1B, when balloon 14 is in a deflated state, the edges 17 of folded groove 16 cooperate to form a compartment 19 holding a therapeutic agent 18. The edges 17 may touch or be close together and may be held together by, for example, an adhesive, biodegradable or bioerodable sutures or stitching, or some other means by which the edges may be held closely together or touching during balloon delivery but which will allow the edges to separate upon balloon expansion. The width, pitch, pitch angle, and depth of folded groove 16 on balloon 14 will vary depending upon the particular application.

Figure 1C:
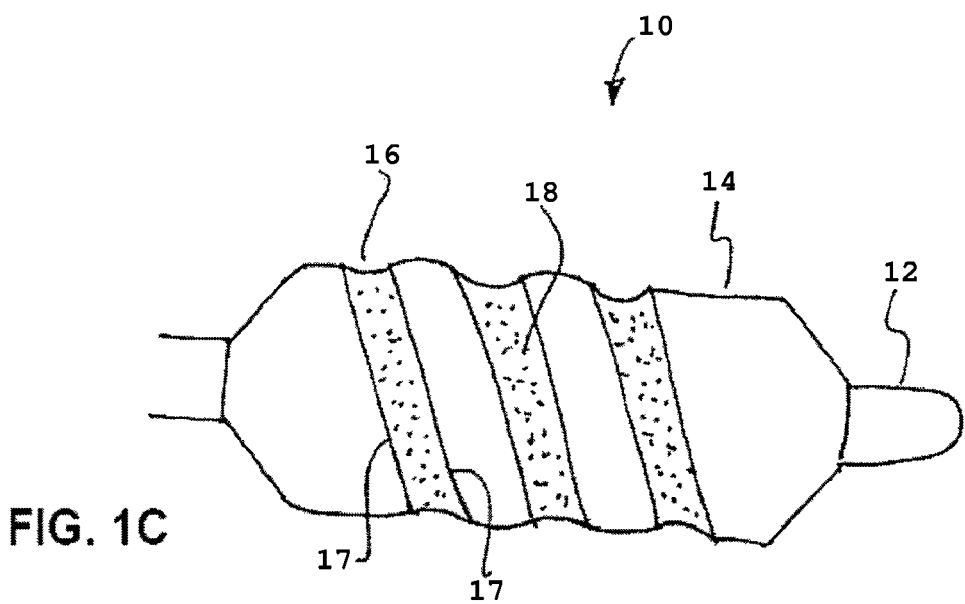

In operation, balloon 14 is inserted into the body via a catheter. Because therapeutic agent 18 is contained within folded groove 16, therapeutic agent 18 is protected while balloon 14 is being guided to the target site. As shown in FIG. 1C, at the target site, balloon 14 is inflated, causing folded groove 16 to widen and causing edges 17 of folded groove 16 to separate, thus exposing therapeutic agent 18 for release at the target site.

Figure 2A:
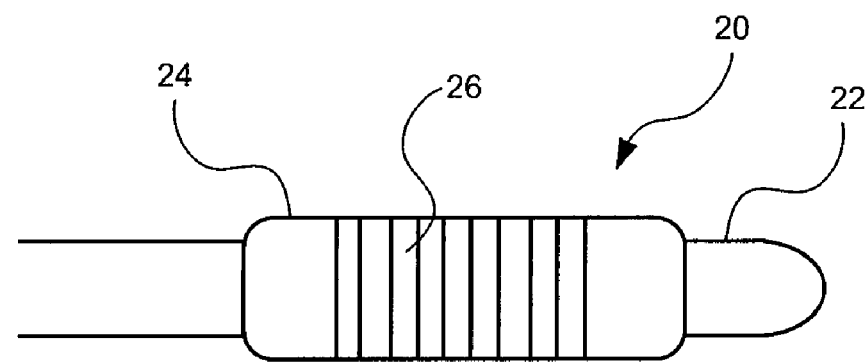
FIGS. 2A and 2B show a catheter device according to another embodiment.
Figure 2B:
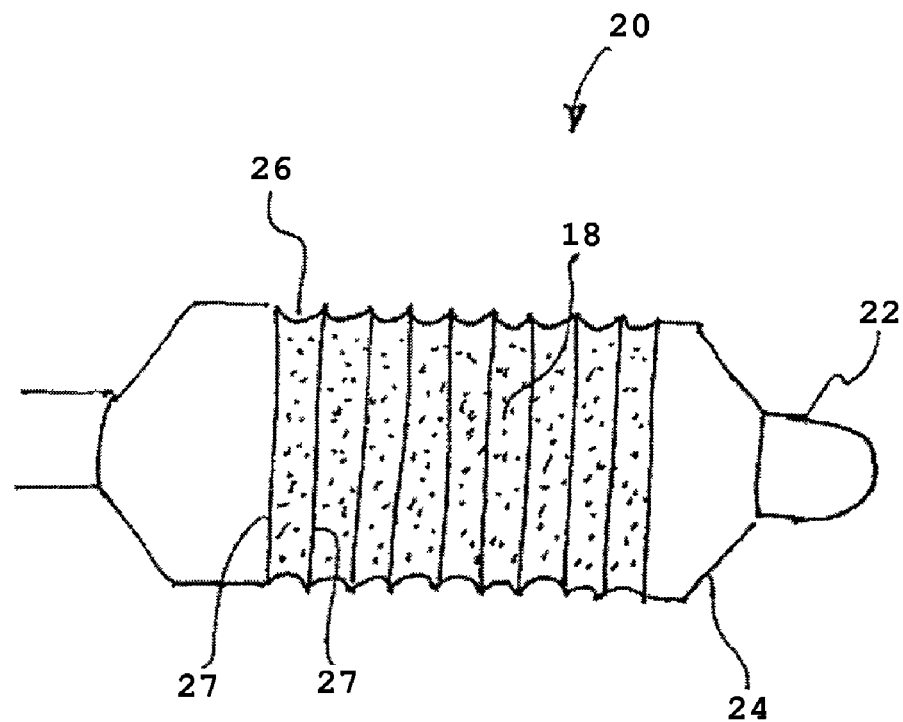

In another example, referring to the embodiment shown in FIGS. 2A and 2B, a catheter device 20 comprises a balloon 24 mounted on an elongate shaft 22. Balloon 24 has a plurality of folded grooves 26 extending in a radial fashion around the circumference of balloon 24. When balloon 24 is in a deflated state, the edges 27 of grooves 26 cooperate to form compartments holding therapeutic agent 18. The edges 27 may touch or be close together and may be held together as described above. The cross-section of a groove 26 may be similar to that shown in FIG. 1B. The number, width, pitch, and depth of folded grooves 26 on balloon 24 will vary depending upon the particular application.

In operation, balloon 24 is inserted into the body via a catheter. Because therapeutic agent 18 is contained within folded groove 26, therapeutic agent 18 is protected while balloon 24 is being guided to the target site. As shown in FIG. 2B, at the target site, balloon 24 is inflated, causing groove 26 to widen and causing edges 27 of folded groove 26 to separate, thus exposing therapeutic agent 18 for release at the target site.

In certain embodiments of the invention, the configuration of the balloon and the therapeutic agent reservoirs can be controlled such as to allow release of the therapeutic agent only at the desired time. For example, the device may be designed such that a certain pressure within the balloon is required for the folds to open and release the therapeutic agent. In this way, the therapeutic agent can be held in the folds while the device is delivered through the blood vessel to the target site. Then, at the target site, the balloon is inflated, and when the balloon reaches the pressure and/or diameter at which the folds are designed to open, the therapeutic agent will be released. In this way, for example, the therapeutic agent release can be controlled such that it is released only if the balloon is in contact with or in close proximity to the vessel wall. This helps to prevent loss of the therapeutic agent during catheter placement and balloon inflation. Also, because deflation of the balloon can, in some instances, stop or substantially reduce therapeutic agent release, certain embodiments of the invention can control the duration of release after the initial release of therapeutic agent.

Figure 3A:
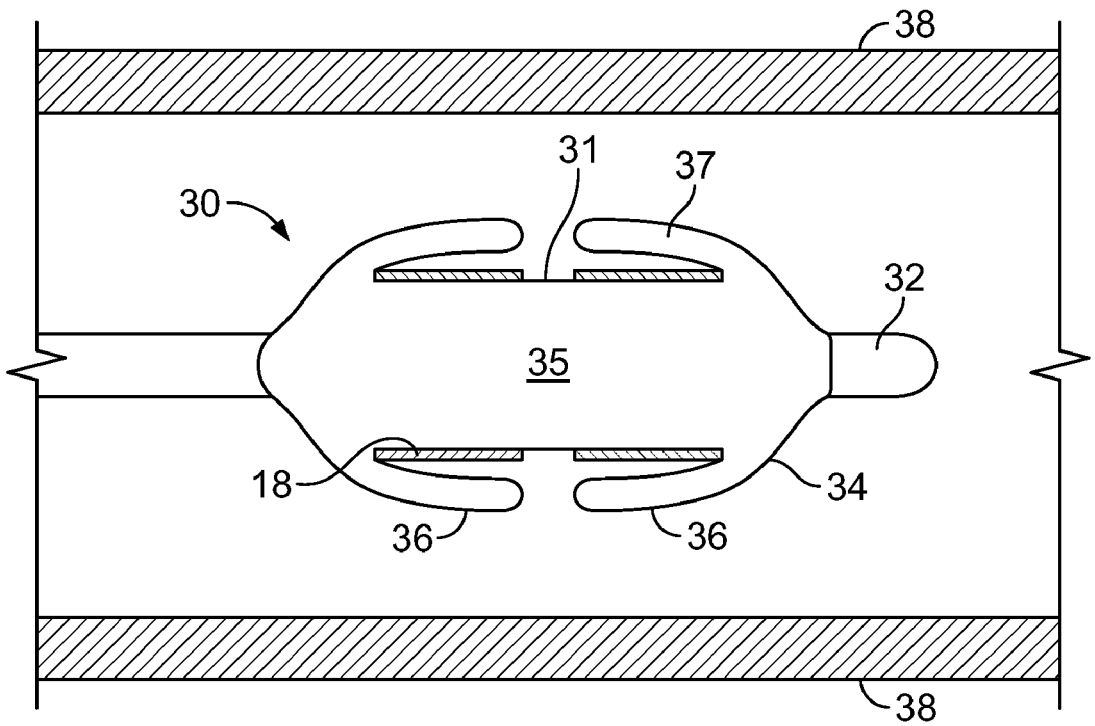
FIGS. 3A and 3B show a catheter device according to another embodiment.

In certain embodiments, the balloon comprises one or more lobes (e.g., a wing, a bi-fold wing, a T-wing, or a cuff) that forms the one or more folds. For example, referring to the embodiment shown in FIGS. 3A and 3B, a catheter device 30 comprises a balloon 34 mounted on an elongate shaft 32. Balloon 34 comprises a cylindrical main body 31, which is coated with a therapeutic agent 18, and two circumferential cuff portions 36. When the balloon is in an unexpanded state, cuff portions 36 assume a low profile to allow insertion of the balloon into a catheter and/or blood vessel. The interior 37 of cuff portions 36 are in communication with the inflation chamber 35 of main body 31. As shown in FIG. 3A, when balloon 34 is in a deflated state, cuff portions 36 are folded over balloon 34 such that cuff portions 36 cover therapeutic agent 18. In certain embodiments, only the surfaces of balloon 34 that are covered by cuff portions 36 when in a deflated state are coated with the therapeutic agent.

Figure 3B:
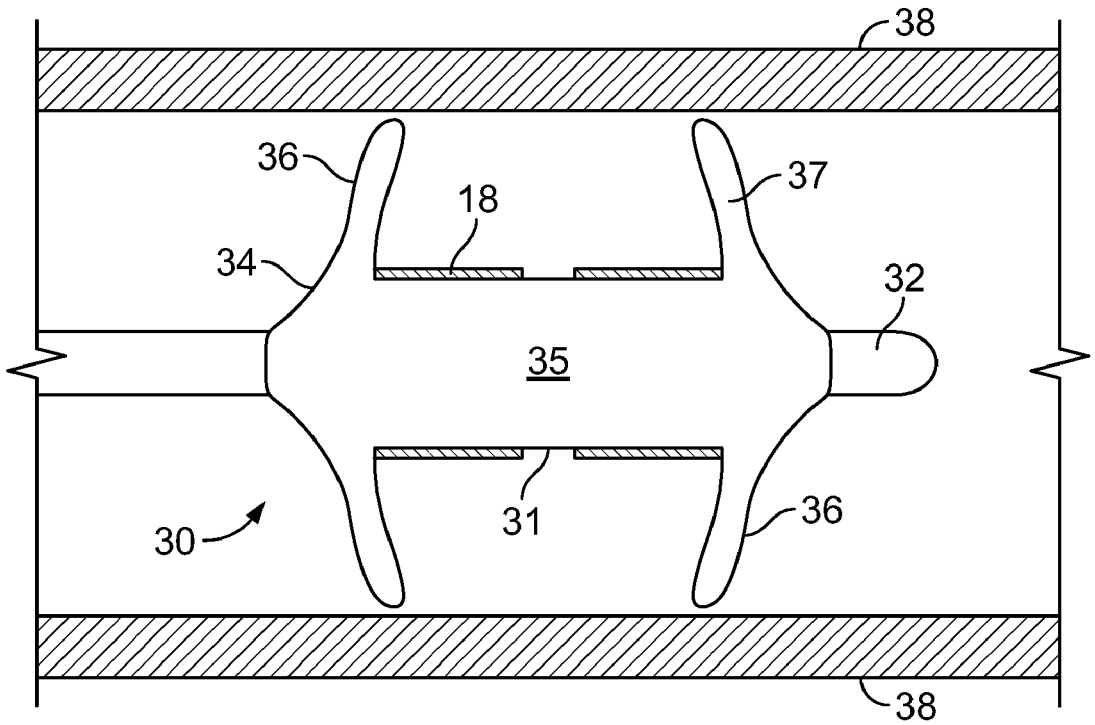

In operation, balloon 34 is inserted into a blood vessel via a catheter. Because cuff portions 36 cover therapeutic agent 18, therapeutic agent 18 is protected while balloon 34 is being guided to the target site. At the target site, as shown in FIG. 3B, balloon 34 is inflated, causing cuff portions 36 to extend outward in a radial direction, thus exposing therapeutic agent 18 for release at the target site. In an example embodiment, when the cuff portions 36 are fully extended radially, each cuff portion has a length of between about ¼ of the entire length of balloon 34 to ½ of the entire length of balloon 34. Also, by extending in a radial direction, cuff portions 36 can also abut against the vessel wall 38 and seal the space between cuff portions 36. In this way, therapeutic agent 18 can be applied to vessel wall 38 while reducing the amount of therapeutic agent 18 washed away downstream by the flow of blood.

In another example, referring to the embodiment shown in FIGS. 4A-4C, a catheter device comprises a balloon 60, which has a plurality of inflatable bi-fold wings 62 and an inflatable central body 64. When the balloon is in an unexpanded state, bi-fold wings 62 assume a low profile to allow insertion of the balloon into a catheter and/or blood vessel. The interior 66 of bi-fold wings 62 are in communication with the inflation chamber 65 of central body 64. As shown in FIG. 4A, when balloon 60 is in a deflated state, a therapeutic agent 18 is sandwiched between the folds of bi-fold wings 62. Also, when balloon 60 is in a deflated state, bi-fold wings 62 circumferentially wrap around central body 64.

In operation, balloon 60 is inserted into the body via a catheter. Because therapeutic agent 18 is sandwiched between the folds of bi-fold wings 62, therapeutic agent 18 is protected while balloon 60 is being guided to the target site. At the target site, as shown in FIG. 4B, balloon 60 is inflated, causing bi-fold wings 62 to extend outward. As shown in FIG. 4C, with further inflation, balloon 60 assumes a more cylindrical shape, in which therapeutic agent 18 is exposed on the outer surface of balloon 60 to facilitate application of therapeutic agent 18 to the body tissue.

In another example, referring to the embodiment shown in FIGS. 5A-5C, a catheter device comprises a balloon 90, which has a plurality of inflatable T-wings 92 and an inflatable central body 94. The interior 96 of T-wings 92 are in communication with the inflation chamber 95 of central body 94. As shown in FIG. 5B, when balloon 90 is in a deflated state, a therapeutic agent 18 coats the inside surfaces of T-wings 92 (i.e., the undersides 99 and stems 98 of T-wings 92).

In operation, balloon 90 is inserted into a patient's body via a catheter. Because therapeutic agent 18 is located on a non-exposed surface of balloon 90, therapeutic agent 18 is protected while balloon 90 is being guided to the target site. As balloon 90 is inflated, T-wings 92 assume a less distinctive shape. As shown in FIG. 5C, as balloon 90 is inflated, T-wings 92 expand outward such that balloon 90 assumes a more cylindrical shape, in which therapeutic agent 18 is exposed on the outer surface of balloon 90 to facilitate application of therapeutic agent 18 to the body tissue.

In some cases, one or more packets containing the therapeutic agent may be disposed within the folds that are created by the lobes of the balloon. The packet is attached to two or more sites on the surface of the balloon at two or more different sites on the packet. As the balloon is expanded, the balloon applies a pulling force on the packet, causing the packet to rupture and allow release of the therapeutic agent.

The walls of the packet may or may not be distinct from the walls of the balloon. In some cases, at least a portion of the packet shares the same wall as the balloon. In some cases, the packet may be manufactured separately from the balloon and then attached to the balloon. In such cases, the walls of the packet may be distinct from the walls of the balloon. The packet may have various three-dimensional shapes suitable for fitting within the folds of the balloon, including rectangular cuboid, cylindrical, spheroid, or ellipsoid shapes. The packet may or may not have an elongate shape. The packet may or may not be completely sealed.

The packet has a tensile rupture strength, which is the amount of stretching force required to rupture the packet. To allow the packet to rupture upon expansion of the balloon, the strength of the attachment between the packet and the balloon will exceed the tensile rupture strength of the packet. The tensile rupture strength of the packet and/or the stretching force applied to the packet may be varied to create a design such that the packets rupture upon expansion of the balloon. For example, adjustments can be made to various parameters, such as the structural, geometric, and/or material characteristics of the packet; the spatial geometry of the attachment sites on the packet; the structural, geometric, and/or material characteristics of the balloon; and the dynamic geometry of the balloon as it expands. For example, the tensile rupture strength of the packet may be reduced by making the packet with thinner walls. In some cases, the packet may be made with a soft and pliable polymeric material to prevent premature rupture of the packet. For example, the packet may be made of polyurethane, especially when the balloon is also made of polyurethane.

The packet may contain a single therapeutic agent or a mixture of different therapeutic agents. In cases where the balloon has a plurality of packets, different packets may contain different therapeutic agents. The therapeutic agent may be provided in any suitable formulation or dosage form, such as capsules or nanoparticles (e.g., albumin-bound paclitaxel, sold as Abraxane® (Astra-Zeneca)). The packet may further contain an excipient material to facilitate delivery of the therapeutic agent. For example, the packet may contain a viscous material for adhering the therapeutic agent to the tissue. Examples of viscous materials which may be suitable for use include bioabsorbable waxes, pastes, binders (e.g., polyvinyl pyrrolidone), plasticizers, gels, proteins (e.g., albumin, fibrinogen, or gelatin), fats, or biodegradable polymers (e.g., glycerol, polylactic acid, or polyglycolic acid).

Figure 6A:
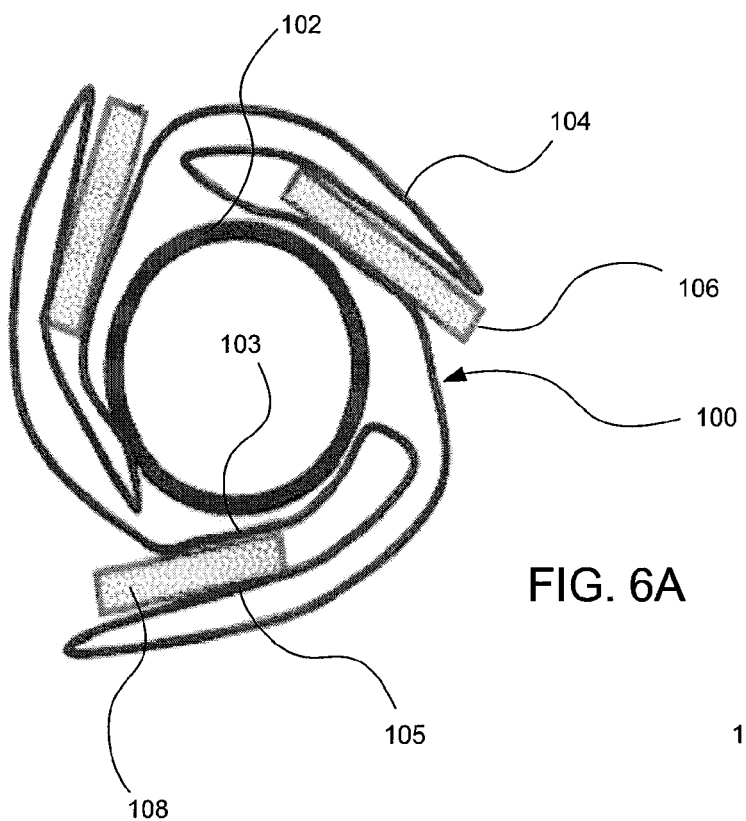
FIGS. 6A and 6B show transverse cross-section views of a balloon according to another embodiment.
Figure 6B:
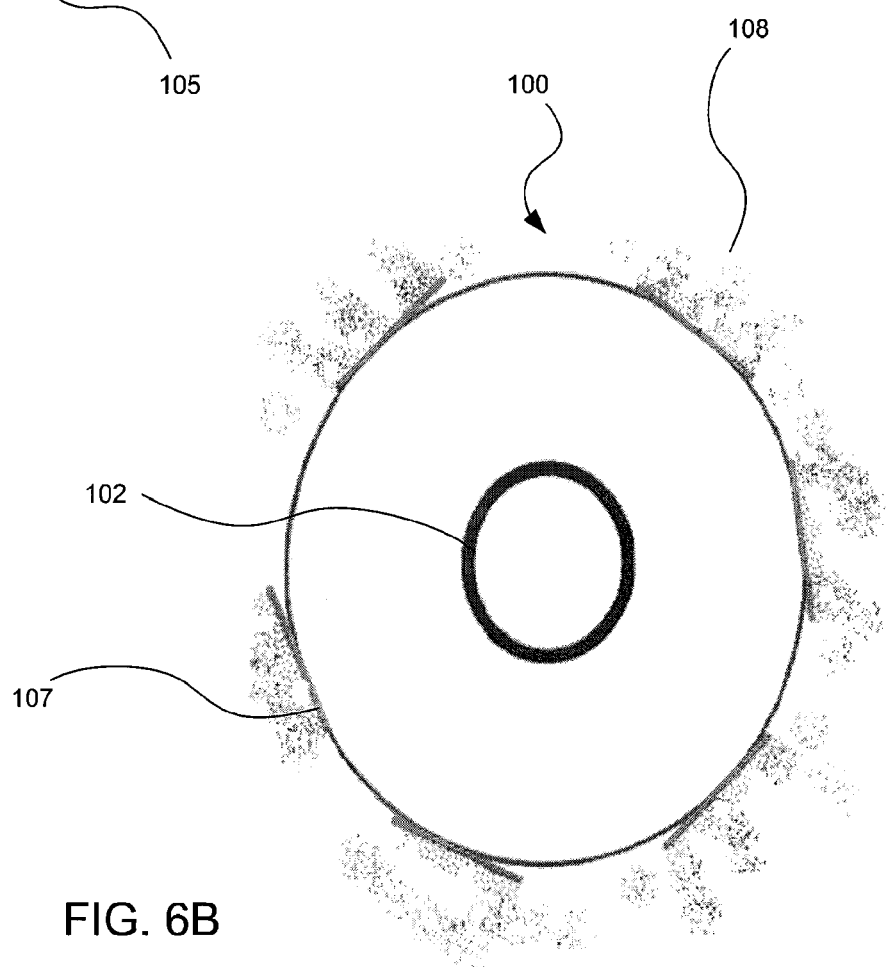

For example, referring to the embodiment shown in FIGS. 6A and 6B (transverse cross-section views), a catheter device comprises an elongate balloon 100 mounted on an elongate shaft 102. Balloon 100 has a plurality of lobes 104 that form one or more folds. Disposed within the folds of balloon 100 are elongate strip-shaped packets 106 that hold a therapeutic agent 108. Strip-shaped packets 106 are oriented parallel to the longitudinal axis of elongate balloon 100. Packets 106 are adhered between a lobe 104 and an adjacent surface of the balloon 100 or between adjacent lobes 104 of balloon 100. As shown here, packets 106 face the balloon surface at its "top" face 103 and "bottom" face 105, which are the sites at which packet 106 is adhered to the balloon surface.

In operation, balloon 100 is inserted into the body via a catheter. Because packets 106 of therapeutic agent are contained within the folds created by lobes 104, the therapeutic agent is protected while balloon 100 is being guided to the target site. As shown in FIG. 6B, upon inflation of balloon 100, lobes 106 expand outward and open the folds. This expansion of lobes 106 pull apart packet 106 at its attachment sites causing packets 106 to rupture. As shown in FIG. 6B, rupture of packets 106 (leavings its remnants 107) allows the release of therapeutic agent 108.

Figure 7:
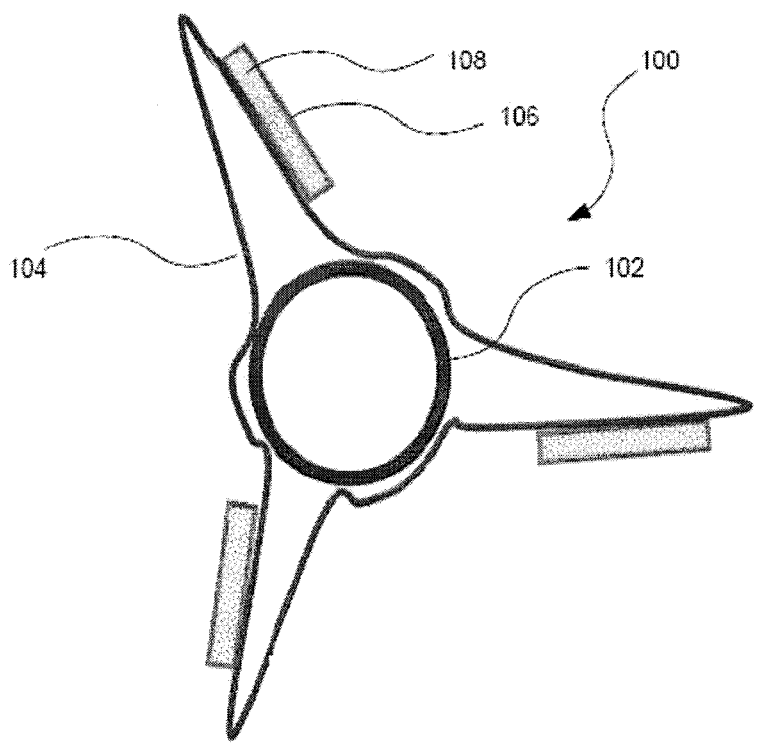
FIG. 7 shows a manufacturing step in the manufacture of a device like that in FIGS. 6A and 6B.

FIG. 7 shows one manner by which balloon 100 in FIG. 6A may be made. With balloon 100 in an uninflated state, lobes 104 are unfolded to expose their sides. An adhesive is applied onto the "top" and "bottom" faces of packets 106. Packets 106 are adhered onto one side of lobes 104. Lobes 104 are then folded over such that the other side of each packet 106 is adhered to an adjacent surface of balloon 100.

Figure 8:
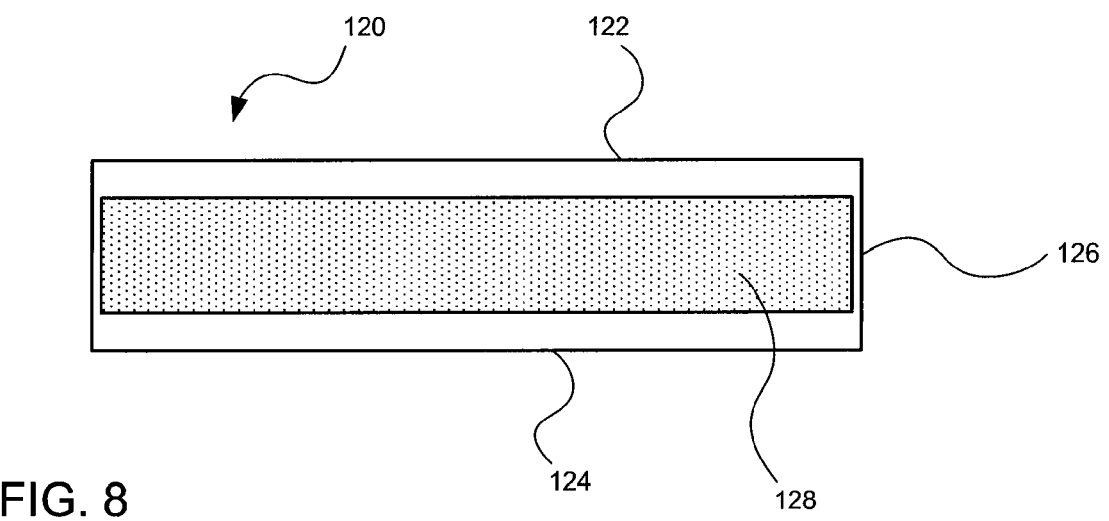
FIG. 8 shows a packet according to an embodiment that can be used with a device like that in FIGS. 6A and 6B.

The packets may be designed in such a way to facilitate their rupture. For example, FIG. 8 shows a rectangular-cuboid shaped packet 120 containing a therapeutic agent 128. Packet 120 has a top face 122, a bottom face 124, and lateral faces 126. The wall of packet 120 is thicker at the top face 122 and bottom face 124, which are the sites of attachment to the balloon, and thinner at the lateral faces 126. Thus, when top face 122 is pulled apart from bottom face 124 as the balloon is inflated, packet 120 will preferentially rupture at the lateral walls 126.

Figure 9:
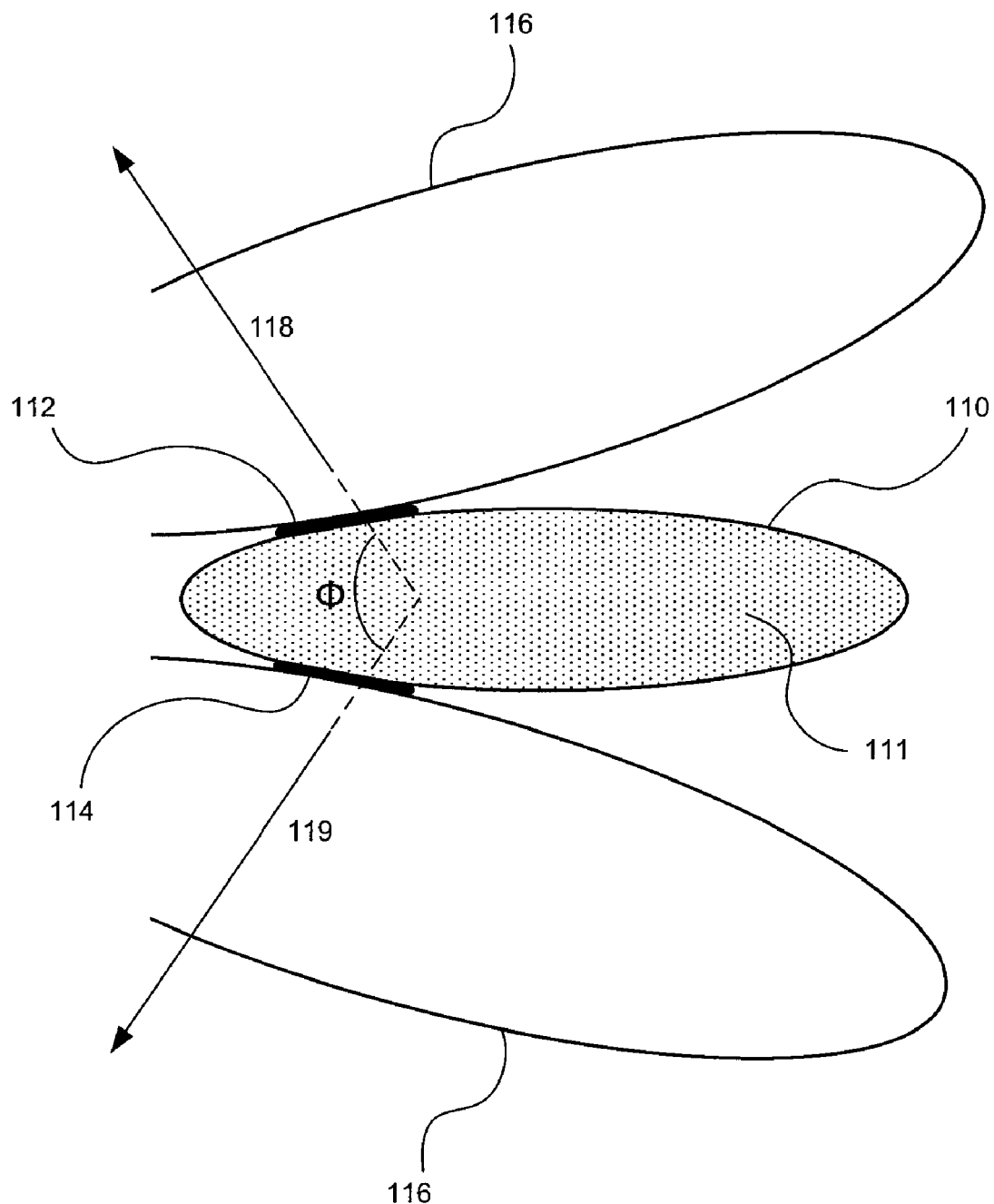
FIG. 9 illustrates the direction of the forces pulling upon a packet.

In the embodiment shown in FIG. 6A, the attachment sites are on substantially opposite faces of packet 106, with the attachment sites being pulled apart in opposite directions when balloon 100 is inflated. However, the attachment sites do not necessarily have to be located on opposite faces or be pulled apart in opposite directions, so long as the forces pulling upon the attachment sites are sufficient to rupture the packets. In some cases, the balloon and/or packets may be designed such that the attachment sites are pulled apart at an angle in the range of 60-180° as the balloon is inflated. To illustrate, FIG. 9 shows an ovoid-shaped packet 110 containing a therapeutic agent 111. Packet 110 is attached to lobes 116 of a balloon at attachment sites 112 and 114. Arrows 118 and 119 represent the direction vector in which lobes 116 will pull on packet 110 as the balloon is inflated. In some embodiments, the angle $\theta$ between these two vectors is in the range of 60-180°, but other angles are also possible.

The use of packets as described herein allows for the containment of the therapeutic agent during manufacturing and/or delivery of the medical device into a blood vessel. Thus, the therapeutic agent is protected from the environment and from early release until the device is at the target site and the balloon is inflated. Also, the use of packets as well as the use of therapeutic agent reservoirs as described above can allow for the use of therapeutic agents (or formulation mixtures thereof) that could not otherwise be used because of lack of adherence to the balloon.

Also, the packets can be designed to protect the therapeutic agent in cases where the device is subjected to a sterilization process. For example, the packets can be sealed or have walls that are thicker or made of a less permeable material to make the packets in-penetrable to the sterilization process. As such, a wider range of sterilizations processes for the device can be made available, even some that may otherwise be harmful to an openly exposed therapeutic agent. For example, if it is desirable to use ethylene oxide to sterilize the device but the therapeutic agent is sensitive to ethylene oxide, the packets could be designed to be impermeable to ethylene oxide to protect the therapeutic agent contained inside. Furthermore, in cases where a vascular stent is crimped onto the balloon, the packets can be designed to withstand the forces that are applied during crimping of the stent onto the balloon.

The number of lobes and packets may vary, with possibly multiple packets per lobe. Also, the shape of the lobes can vary. For example, the lobes may be configured like the cuffs or wings shown in FIGS. 3A, 3B, 4A, 4B, 5A, and 5B, with the packets being adhered in the places where the therapeutic agent is shown in these figures.

In certain embodiments, the therapeutic agent is provided as a plurality of bulk masses that are disposed within the folds. The bulk masses of therapeutic agent are discrete, i.e., distinct and detached from each other. The bulk masses of therapeutic agent may have any of various three-dimensional shapes suitable for fitting within the folds of the balloon, including rectangular cuboid, cylindrical, spheroid, or ellipsoid shapes. For example, the bulk masses of therapeutic agent may have an elongate shape in the form of rods, ribbons, strips, or fibers. The balloon may have from 10 to 1000 individual bulk masses of therapeutic agent disposed thereon, but other quantities are also possible depending upon the particular application.

The bulk masses of therapeutic agent may be thicker than the typical thickness of conventional drug coatings on balloons. For example, the bulk masses may have a thickness in the range of 10-150 μm, and in some cases, in the range of 25-100 μm, but larger or smaller thicknesses are also possible. The length of each bulk mass may be as small as 0.25 mm or smaller, and may range up to the entire length of the balloon (e.g., 8 mm for coronary artery balloons or 200 mm for peripheral artery balloons) or longer. In cases where paclitaxel is the therapeutic agent, each bulk mass may contain, for example, from 0.1 to 100 μg of paclitaxel.

Figure 10:
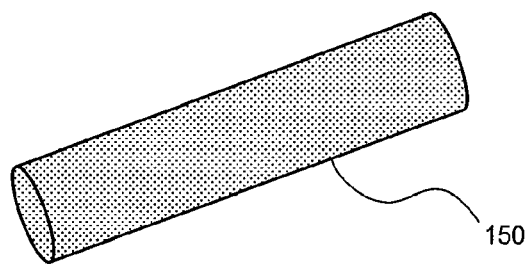
FIG. 10 shows a bulk mass of a therapeutic agent according to an embodiment that can be used with a device like that in FIGS. 11A and 11B.
Figure 11A:
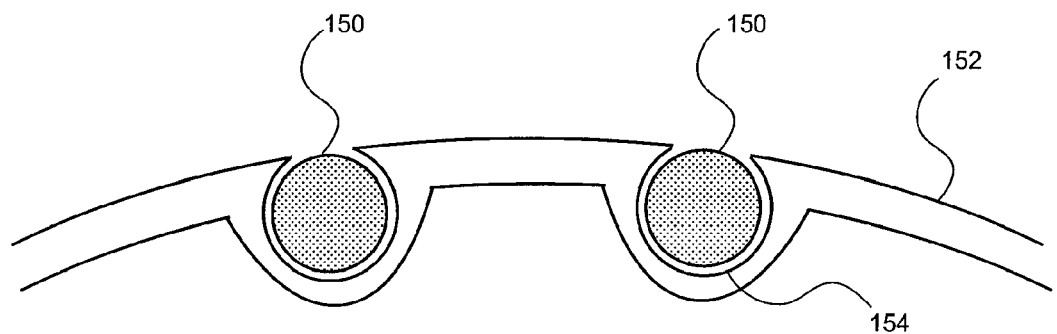
FIGS. 11A and 11B show transverse cross-section views of a portion of a balloon wall according to an embodiment.

For example, referring to the embodiment shown in FIG. 10, a bulk mass of therapeutic agent has the shape of a rod 150. Referring to the embodiment shown in FIG. 11A (transverse cross-section view), the wall 152 of an elongate balloon is creased into folds 154 that extend longitudinally along the length of the balloon. Folds 154 contain the rods 150 of therapeutic agent. The folds may have edges similar to those described above with respect to FIG. 1B.

Figure 11B:
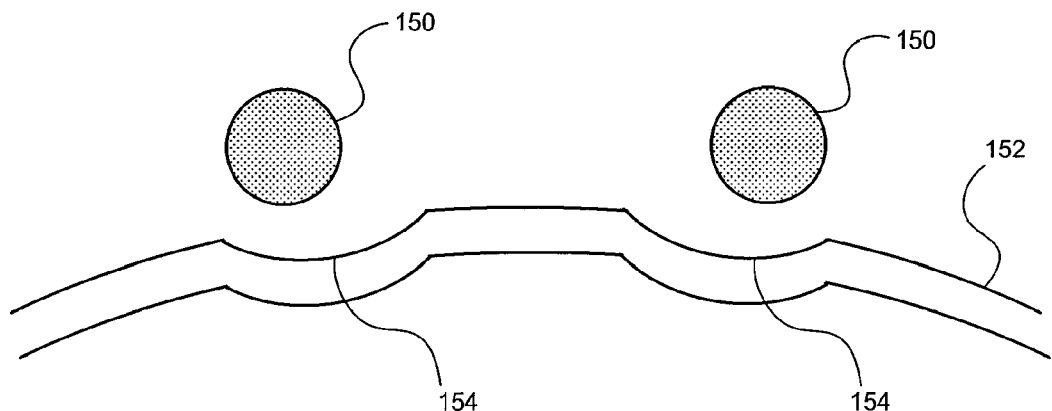

In operation, the balloon is inserted into the body via a catheter. Because rods 150 of therapeutic agent are contained within folds 154, rods 150 are protected while the balloon is being guided to the target site. As shown in FIG. 11B, when the balloon is delivered to the target site and inflated, folds 154 open such that rods 150 are released from the balloon.

The bulk mass of therapeutic agent may be formed in any suitable way known in the art. For example, rods 150 may be made by preparing a liquid formulation of the therapeutic agent in a solvent. The liquid formulation of therapeutic agent is then applied into folds 154 of the balloon (e.g., by spraying or dip coating). The liquid formulation is then dried such that the solid residue of therapeutic agent is cast into the shape of fold 154 (i.e., as a rod shape). The shaping may be aided by crystallization of the therapeutic agent as it is dried. Also, shaping may be aided by adding other materials, such as binders, plasticizers, polymeric materials, metallic materials, or radiocontrast agents into the liquid formulation. Alternatively, rods 150 may be made separately and then inserted into folds 154 of the balloon. The bulk masses may be, for example, polymeric, organic, and/or metal, and may be biostable, bioresorbable, bioerodable, or biodegradable. In some embodiments, the rods 150 of therapeutic agent may be localized to particular segments of the balloon. This feature may be useful in avoiding delivery of the therapeutic agent to segments of an artery containing calcified lesions. In some cases, the bulk masses may be implantable in the target tissue (e.g., blood vessel wall).

Figure 12A:
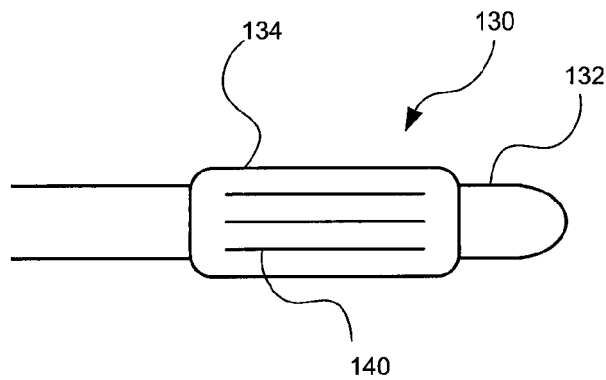
FIGS. 12A-12E show a catheter device according to another embodiment.
Figure 12B:
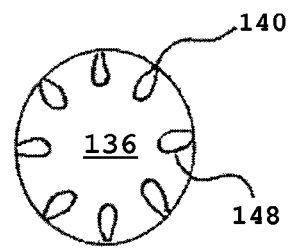
Figure 12C:
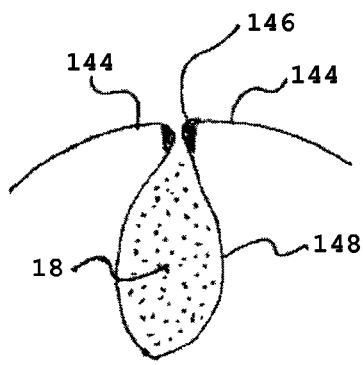

In certain embodiments, the edges of a fold may come together to form a sealed compartment for containing the therapeutic agent. For example, referring to the embodiment shown in FIGS. 12A-12E, a catheter device comprises a balloon 134 mounted on an elongate shaft 132. In its interior, balloon 134 has an inflation chamber 136, and on its exterior, balloon 134 has a plurality of longitudinal folds 140. As seen in FIGS. 12B and 12C, the edges 144 of folds 140 meet to create a compartment 148 for containing a therapeutic agent 18. Furthermore, the edges 144 of folds 140 can each have an adhesive strip 146 that are mutually aligned with each other. The edges 144 of folds 140 can be joined together by contact between adhesive strips 146 such that therapeutic agent 18 is sealed within compartment 148.

Figure 12D:
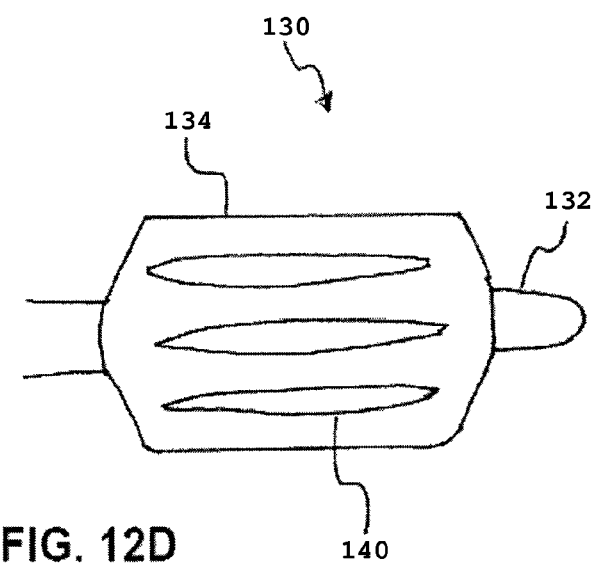
Figure 12E:
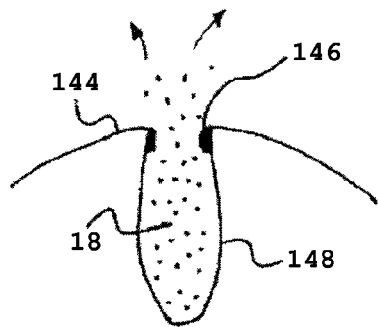

In operation, balloon 134 is inserted into a patient's body via a catheter. Because therapeutic agent 18 is sealed within compartments 148, therapeutic agent 18 is protected as balloon 134 is being guided to the target site. At the target site, balloon 134 is inflated, causing adhesive strips 146 to pull apart. As shown in FIGS. 12D and 12E, as balloon 134 continues to expand, adhesive strips 146 detach such that edges 144 open, allowing therapeutic agent 18 to be released from compartment 148. In an alternate embodiment, the edges 144 of folds 140 can be sealed by other means, such as laser welding, heat setting, or by other holding means such as biodegradable or bioerodable sutures or stitching.

Figure 13A:
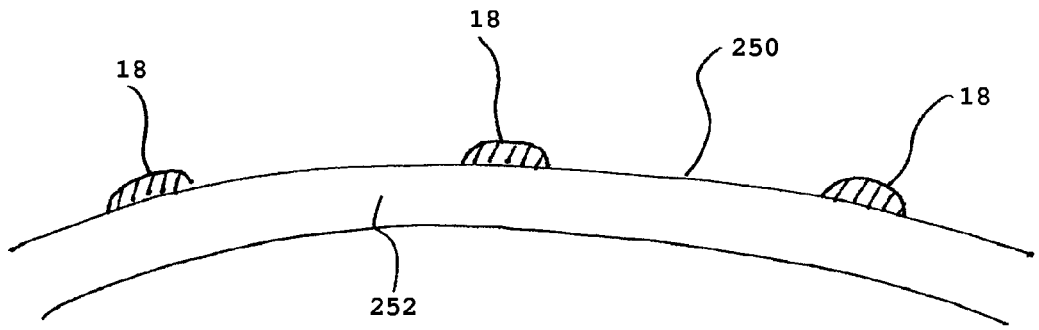
FIGS. 13A-13C show a balloon during various stages of a manufacturing process according to an embodiment.
Figure 13B:
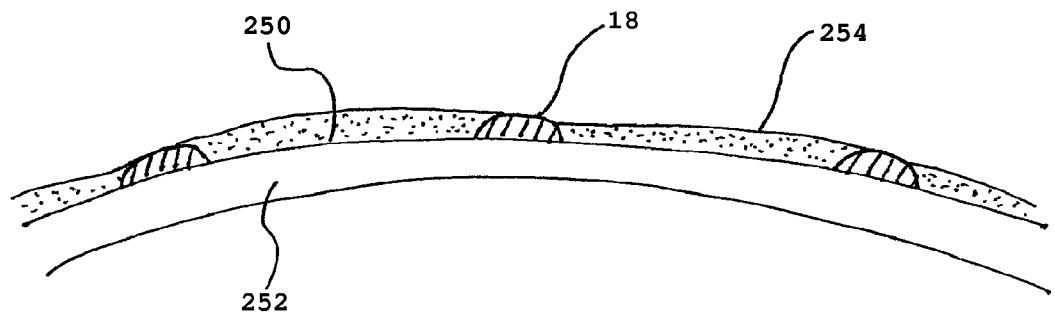
Figure 13C:
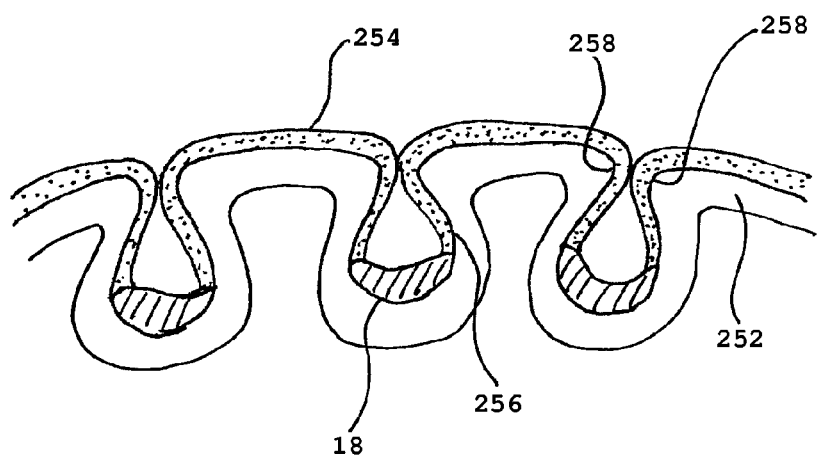

Folds containing the therapeutic agent may be formed in various ways. One way of making folds in the balloon is shown with reference to FIGS. 13A-13C, which show transverse cross-sections of a balloon (having a balloon wall 252). Referring to FIG. 13A, a therapeutic agent 18 (either free or formulated with a carrier material) is deposited on the surface 250 of the balloon as stripes that are oriented substantially longitudinally along the balloon. Referring to FIG. 13B, the areas between the stripes of therapeutic agent 18 is coated with a hydrophobic layer 254 formed of a hydrophobic material (e.g., hydrophobic polymers, such as styrene-isobutylene-styrene (SIBS) block copolymers or styrene-ethylene/butylene-styrene (SEBS) block copolymers). Referring to FIG. 13C, the balloon is folded around the stripes of therapeutic agent 18 to create folds 256 which contain the stripes of therapeutic agent 18. The edges 258 of folds 256 meet such that therapeutic agent 18 is sealed within folds 256. The hydrophobic material can help retard fluid penetration to slow or prevent the release of therapeutic agent until the desired time.

Therapeutic agent 18 may be released from folds 256 upon inflation of the balloon at the target site, which causes the edges 258 of folds 256 to pull apart, allowing the release of therapeutic agent 18. Alternatively, the edges 258 of folds 256 do not pull apart and therapeutic agent 18 is released by diffusion through hydrophobic layer 254.

In certain embodiments, the balloon is designed such that the folds open when the balloon reaches a certain pressure or a certain expanded diameter, such as when the balloon is close to abutting against the wall of a blood vessel (i.e., the internal diameter of the blood vessel). In certain embodiments, when the balloon is inflated and as the folds open, the folds form a protruding structure that projects outwardly from the main body of the balloon.

Medical devices of the present invention may also include a vascular stent mounted on the balloon. The vascular stent may be any of those known in the art, including those with or without coatings that elute a therapeutic agent. The stent may also be biostable, bioerodable, or biodegradable.

The balloons of the present invention may also be coated with a low-molecular weight carbohydrate, such as mannitol. The carbohydrate may be a separate coating or be blended with the therapeutic agent. The balloons of the present invention may also be coated with a radiocontrast agent (ionic or non-ionic), such as iopromide. The contrast agent may be a separate coating or be blended with the therapeutic agent.

The therapeutic agent used in the present invention may be any pharmaceutically-acceptable agent such as a drug, a non-genetic therapeutic agent, a biomolecule, a small molecule, or cells. Example drugs include anti-proliferative agents or anti-restenosis agents such as paclitaxel, sirolimus (rapamycin), tacrolimus, everolimus, and zotarolimus.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl) ethyleneglycol-N,N,N',N'-tetraacetic acid and mixtures thereof; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; structural protein (e.g., collagen) cross-link breakers such as alagebrium (ALT-711); any combinations and pro-drugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMP's are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin⁻) cells including Lin⁻CD34⁻, Lin⁻CD34⁺, Lin⁻cKit⁺, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells. Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. A medical device comprising:
   a catheter;
   a balloon mounted on the catheter, the balloon comprising a fold that meets at the edges to form a compartment, wherein the fold is sealed at the edges by an adhesive, by laser welding, by heat setting, or by stitchings or sutures that are biodegradable or bioerodable; wherein the compartment opens upon expansion of the balloon; and
   a therapeutic agent disposed within the compartment, wherein opening of the compartment upon expansion of the balloon allows the release of the therapeutic agent.

2. The medical device of claim 1, wherein the fold is oriented longitudinally on the balloon.

3. The medical device of claim 1, wherein the edges of the fold are sealed by an adhesive.

4. The medical device of claim 1, further comprising adhesive strips on the edges, wherein the fold is sealed by contact between the adhesive strips.

5. The medical device of claim 1, wherein the edges of the folds are sealed by laser welding.

6. The medical device of claim 1, wherein the edges of the folds are sealed by heat setting.

7. The medical device of claim 1, wherein the edges of the folds are sealed by stitchings or sutures that are biodegradable or bioerodable.

8. A method of medical treatment, comprising:
   inserting a medical device of claim 1 into a patient's body;
   inflating the balloon to open the sealed compartment; and
   releasing the therapeutic agent from the sealed compartment.

9. The method of claim 8, wherein the fold is oriented longitudinally on the balloon.

10. The method of claim 8, wherein the edges of the fold are sealed by an adhesive.

11. The method of claim 8, further comprising adhesive strips on the edges, wherein the fold is sealed by contact between the adhesive strips.

12. The method of claim 11, wherein inflating the balloon causes the adhesive strips to detach.

13. The method of claim 8, wherein the edges of the folds are sealed by laser welding.

14. The method of claim 8, wherein the edges of the folds are sealed by heat setting.

15. The method of claim 8, wherein the edges of the folds are sealed by stitchings or sutures that are biodegradable or bioerodable.

* * * * *